(12) United States Patent
Chen et al.

(10) Patent No.: US 7,064,833 B2
(45) Date of Patent: Jun. 20, 2006

(54) DOUBLE PATH MICRODROP OPTICAL BIOMETRIC SYSTEM

(75) Inventors: Ter-Chin Chen, Taoyuan (TW); Huang-Tzung Jan, Taoyuan (TW); Jeng-Dang Juang, Taipei (TW); Yen-Ming Pang, Taoyuan (TW)

(73) Assignee: Chung Shan Institute of Science and Technology, Taipei (TW)

( * ) Notice: Subject to any disclaimer, the term of this patent is extended or adjusted under 35 U.S.C. 154(b) by 221 days.

(21) Appl. No.: 10/763,273

(22) Filed: Jan. 26, 2004

(65) Prior Publication Data

US 2005/0162652 A1   Jul. 28, 2005

(51) Int. Cl.
*G01N 21/25* (2006.01)
*G01N 21/00* (2006.01)

(52) U.S. Cl. ........................ 356/409; 356/420; 356/432; 356/433; 356/436

(58) Field of Classification Search ................ 356/409, 356/432, 433, 434, 435, 436, 420
See application file for complete search history.

(56) References Cited

U.S. PATENT DOCUMENTS

| 4,240,751 A | * | 12/1980 | Linnecke et al. | ............ 356/409 |
| 4,640,621 A | * | 2/1987 | Rose | ............ 356/434 |
| 4,753,530 A | * | 6/1988 | Knight et al. | ............ 356/73 |
| 6,258,326 B1 | * | 7/2001 | Modlin | ............ 422/102 |

* cited by examiner

*Primary Examiner*—Gregory J. Toatley, Jr.
*Assistant Examiner*—Roy M. Punnoose
(74) *Attorney, Agent, or Firm*—Harness, Dickey & Pierce, PLC

(57) ABSTRACT

A double path microdrop optical biometric system comprises a micro container, a corner cube array, a collimator, a beam splitting device, a light source selector, a detector and a signal comparator unit. It utilizes the beam to penetrate a specimen with specific coloring agent twice. Then, the shade of the beam can be detected so that a signal comparator unit can calculate the absorptance. The required volume of the specimen used in the system is small. The precision will be doubled by the double path design. Its entire optic-electronic system is simple and at low cost. By using the LEDs, it can avoid the use of filter and solve the over-heating problem. Plus, it can execute many bio-chemical tests.

2 Claims, 4 Drawing Sheets

DOUBLE PATH MICRODROP OPTICAL BIOMETRIC SYSTEM

BACKGROUND OF INVENTION

1. Field of the Invention

A double path microdrop optical biometric system is provided for bio-chemical tests. It has the advantages and functions including the required volume of the specimen (or called sample) is small and the precision will be doubled by the double path design. The entire optic-electronic system is simple and at low cost. By using the LEDs (light emitting diodes), it can avoid the use of filter and the over-heating problem. Moreover, the system can execute various bio-chemical tests.

2. Description of the Prior Art

The conventional bio-chemical detecting methods include two methods. One method is to use a detector to measure the change of voltage that is converted from the bio-chemical energy. The other method is to use the testing agent applied on the specimen. For example, a chemical testing agent or testing paper can be used to measure the density of a target object in the specimen. After which, a quantitative analysis can be done by using some optical techniques.

The first method is easy, compact, fast, and no pollution generated by the testing agent or paper. However, its disadvantages include low precision and not suitable for repeated testing.

The second method is good in the quantitative analysis and suitable for mass detection. It is widely used in different automatic detecting equipments in the bio-chemical industry. Also, it is the major method used in current medical and bio-chemical related fields. But, its disadvantages include the testing device is complex, it is not suitable for dynamic testing, it will cause certain pollution from the testing agent, and its operation is complicated. The basic principle of the optical technique is to measure the absorption as a scale to determine the density of a specific colored object in the specimen. Furthermore, it can be classified into the following methods, such as colorimetric analysis method, spectral analysis method, fluorescent analysis method, turbidity analysis method, etc. The devices about all these methods are quite similar to the conventional spectrometer.

The current commercial spectrometer for bio-chemical testing has many kinds. The large spectrometer is expensive and occupies a huge space. However, the micro spectrometer is light-weighted, small, fast, easy to operate, suitable for mass detection and non-expensive. But, its precision and sensitivity is not good due to the technical limitation of its micro detector. So, it is still not suitable for most bio-chemical testing.

Referring to FIG. 1, it illustrates the structure of a conventional micro spectrometer. It contains two parts, namely the optical system and the electrical system (not shown). The optical system includes a traditional light source having the tungsten filament 91, an condenser 92, a slit 93, an self-focusing blazed reflection grating 94, a detector 95. The traditional light source 91 provides an enough light (or beam) for the micro spectrometer and will cover the wavelength range of the detector 95. The condenser 92 can collected the incoming light into the micro spectrometer. Also, the numerical aperture (N.A.) value should match with the one of the used fiber optics. The function of the corner cube array 94 is to separate the light with different wavelength ranges and to converge the reflected lights to the detector 95. The detector 95 can detect the light intensity and distribution and then converted into electrical signals for further analog output processing.

No matter the conventional spectrometer is the large one or the micro one, the container must be the standard rectangular quartz made container (the bottom is one centimeter square and the depth is one centimeter, so the volume is 1 cc). Therefore, the require volume is relative large.

Assume that the user is located in an area or country where it is under the danger of Severe Acute Respiratory Syndrome (briefly called SARS hereafter) virus. If the user (of a medical organization) needs to collect the sputum of a patient, the user has to collect at least 1 cc to conduct a bio-chemical testing. In case the user only collects 0.5 cc of the patient's sputum, the test cannot be done by the conventional spectrometer because the volume is fewer than the require minimum 1 cc. Hence, the user will miss the best time for determine whether this patient is a SARS patient or not. It not only is disadvantageous for the patient, but also increases the uncertainty and panic for the society.

However, if the user simply reduces the required volume down to 0.5 cc, it will cause another problem that the sensitivity of the entire system becomes one half of the original one. Therefore, the testing becomes unreliable.

Besides, because different coloring agents have different light absorption characteristics, an additional filter has to be added on the conventional light source so that a particular wavelength range can be selected. However, after using the filter for a long period, it will cause the over-heating problem.

Thus, the disadvantages of the conventional spectrometer can be summarized as follows:

[1] the required volume of the specimen is relative large;
[2] the entire optical system is complex and expensive;
[3] the sensitivity of one-path penetration through the specimen is low; and
[4] the conventional tungsten-typed light source needs another filter that causing the over-heating problem.

SUMMARY OF THE INVENTION

The primary object of the present invention is to provide a double path microdrop optical biometric system. In which, the required volume of the specimen is small and the precision will be doubled by the double path design.

The next object of the present invention is to provide a double path microdrop optical biometric system. Its entire optic-electronic system is simple and at low cost.

Another object of the present invention is to provide a double path microdrop optical biometric system. By using the light emitting diodes (briefly called LED hereafter), it can avoid the use of filter and solving the over-heating problem.

Still another object of the present invention is to provide a double path microdrop optical biometric system. In which, it can execute many bio-chemical tests.

In order to achieve the above-mentioned objects, a technical solution is provided. It is a double path microdrop optical biometric system comprising:

a micro container having a predetermined depth and a circular recess with a predetermined diameter for receiving a specimen said micro container having a first end and a second end;

a corner cube array disposed near the first end of said micro container, said corner cube array having several micro corner cube so as to reflect an incoming beam back along its original path of said incoming beam;

a collimator disposed at a position outside said second end of said micro container;

a beam splitting device having a cube beamsplitter, an input fiber, an output fiber and a two-way fiber;

a light source selector for providing a first beam having a predetermined wavelength range and intensity; said light source selector including an electrical switch, a LED array having a plurality of different colored LEDs, a plurality of middle fibers, and a light coupler to guide a selected colored light into the input fiber so that the first light beam having a desired wavelength;

a detector for detecting a final intensity of a received beam; and a signal comparator unit for comparing said detected final intensity of said specimen with a reference intensity so that an absorptance of said specimen can be calculated;

wherein said input fiber guides the first beam passing through said cube beamsplitter of said beam splitting device and then through said two-way fiber to arrive to said collimator so as to expand as a second beam having another diameter approximately equal to said predetermined diameter, then said second beam continues to penetrate said micro container and becomes as a third beam, after reflecting by said corner cube array and passing through said micro container again, a fourth beam is obtained; after passing through said collimator, said fourth beam becomes a collected fifth beam; said fifth beam enters said two-way fiber to arrive to said cube beamsplitter of said beam splitting device and then to be reflected aside into said output fiber and finally to said detector so that said signal comparator unit can calculate an absorptance of said specimen.

DETAILED DESCRIPTION OF THE PREFERRED EMBODIMENT

Figure 1:
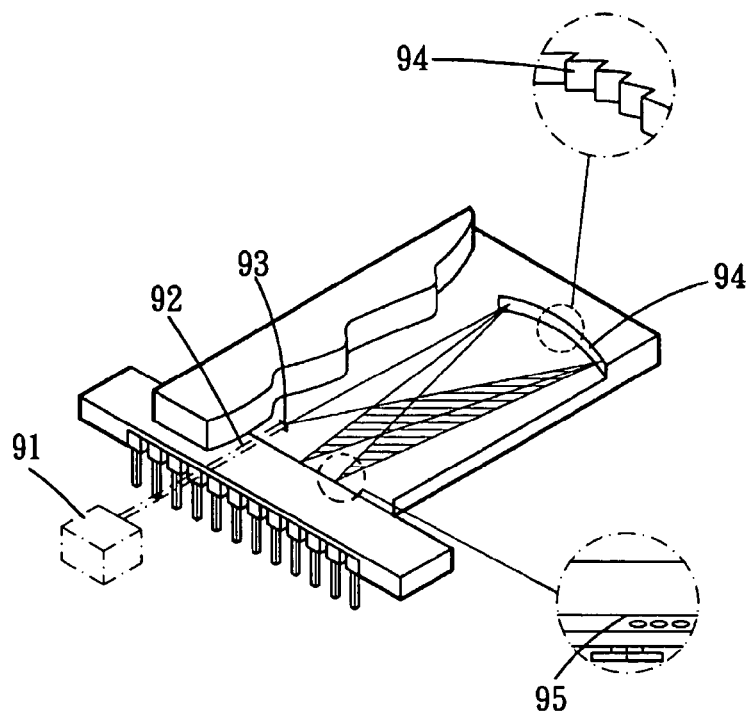
FIG. 1 is a perspective view of a conventional micro spectrometer.
Figure 2:
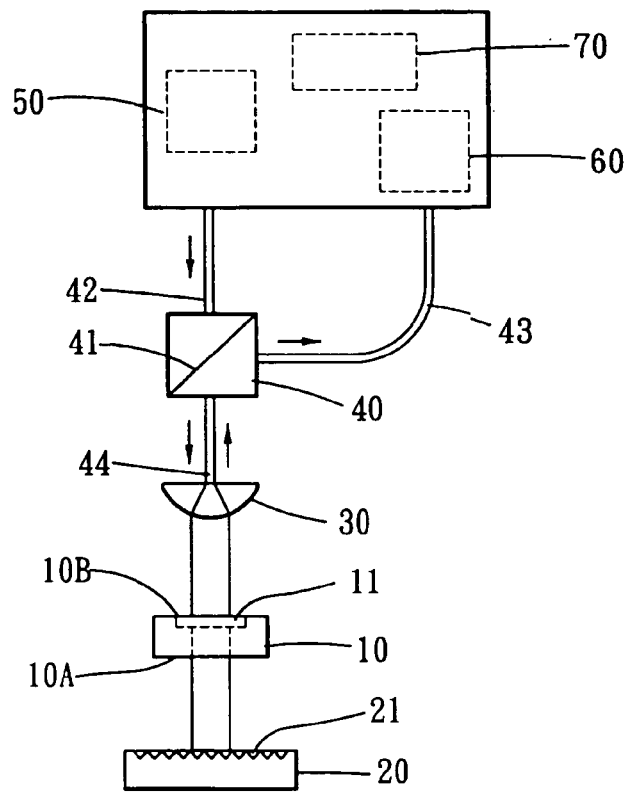
FIG. 2 is a schematic diagram of the system of the present invention.
Figure 3:
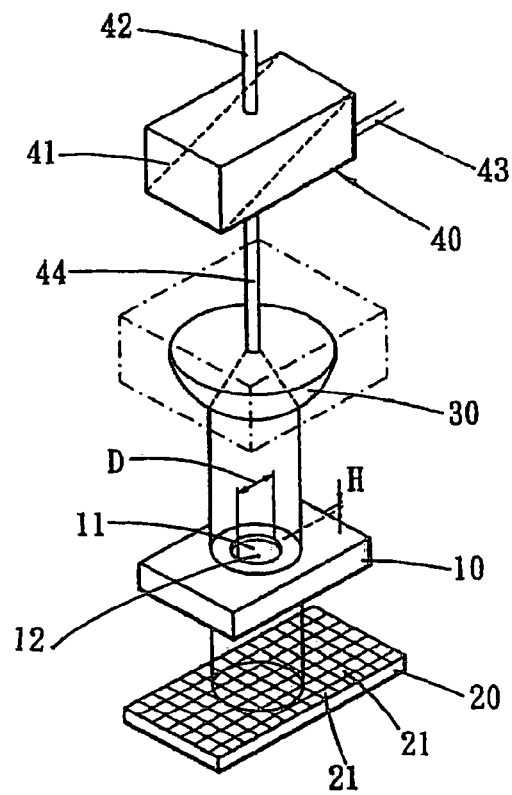
FIG. 3 is a perspective view showing the optical structure of the present invention.
Figure 4:
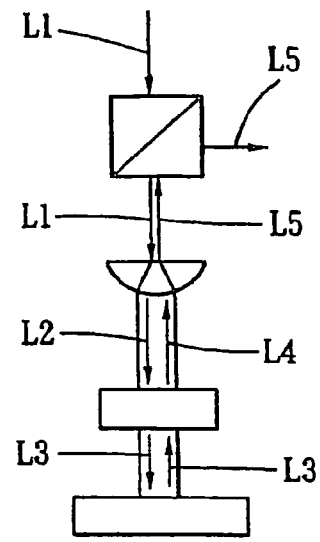
FIG. 4 is a schematic view illustrating the beam.

Referring to FIGS. 2 to 4, the present invention relates to a double path microdrop optical biometric system. It comprises: a micro container 10, a corner cube array 20, a collimator 30, a beam splitting device 40, a light source selector 50, a detector 60 and a signal comparator unit 70.

With regard to the micro container 10, it has a circular recess 11 with predetermined depth H and with a predetermined diameter D for receiving a specimen 12. The micro container 10 has a first end 10A and a second end 10B.

The corner cube array 20 is disposed near the first end 10A of the micro container 10. This corner cube array 20 has several micro corner cube 21 so as to reflect an incoming beam back along its original path of the incoming beam.

The collimator 30 is disposed at a position outside the second end 10B of the micro container 10.

The beam splitting device 40 has a cube beamsplitter 41, an input fiber 42, an output fiber 43, and a two-way fiber 44.

The light source selector 50 is used for providing a first beam L1 that has a predetermined wavelength range and intensity. The light source selector 50 includes an electrical switch 51, a LED array 52 that has a plurality of different colored LEDs, a plurality of middle fibers 53, and a light coupler 54 to guide a selected colored light into the input fiber 42 so that the first light beam L1 having a desired wavelength. Therefore, there are many wavelength ranges that can be chosen. Its advantage is to allow the user to execute one of many different bio-chemical tests by selecting a suitable wavelength range, such as to detect the density of blood sugar, the density of a specific influenza virus, etc. Thus, this invention is multi-functional.

Concerning the detector 60, it is used for detecting a final intensity of a received beam.

The signal comparator unit 70 is used for comparing the detected final intensity of the specimen 12 with a reference intensity so that a absorptance of the specimen 12 can be calculated.

Therefore, the input fiber 42 guides a first beam L1 passing through the cube beamsplitter of the beam splitting device 40 and then through the two-way fiber 44 to arrive to the collimator 30 so as to expand as a second beam L2 having another diameter approximately equal to said predetermined diameter D; then the second beam L2 continues to penetrate the micro container 10 and becomes a third beam L3 (The third beam L3 is weaker than the second beam L2 because some of the beam is absorbed by the specimen 12). After reflecting by the corner cube array 20 and passing through the micro container 10 again, a fourth beam L4 (the fourth beam L4 is weaker than the third beam L3) is obtained. After passing through the collimator 30, the fourth beam L4 becomes a collected fifth beam L5. The fifth beam L5 enters the two-way fiber 44 to arrive to the cube beamsplitter 41 of the beam splitting device 40 and then to be reflected aside into the output fiber 43 and finally to the detector 60 so that the signal comparator unit 70 can calculate an absorptance of the specimen 12.

In addition, the micro container 10 can be an elongated transparent plastic plate and said circular recess 11 has a diameter (D) between 4 to 6 mm and a depth (H) between 0.1 to 0.5 mm.

About the principle of this invention, once the beam penetrates the specimen 12 one time, the passing beam will be weakened. Thus, if it penetrates the specimen 12 twice, the total amount of decaying will be doubled. So, by measuring the amount of decaying, the absorptance can be determined.

In this system, the specimen 12 contains a specific colored material/agent that already chemically reacted with an object that the user wants to measure. The shade of the colored specimen is proportional to the degree of density of such object. By establishing the relationship between the shade and the density of the colored specimen after chemically reacted with a suitable coloring agent, the density of the specimen 12 can be determined by detecting its actual shade of the specimen 12. In a bio-chemical test, usually a suitable coloring agent will be added to react with the object that we want to measure. Therefore, the shade of such color means the density of the object. The shade can be precisely measured by the voltage output of the detector. Of course, a graph about such relationship between the shade and the density can be established.

In this embodiment, the detailed specification about all the related parts of this invention can be summarized as follows:

The diameter of the fiber (including the input fiber, output fiber, the two-way fiber and so on) is 1.00 mm. The Numeric Aperture (NA) value of all these plastic fiber is 0.44.

Figure 5:
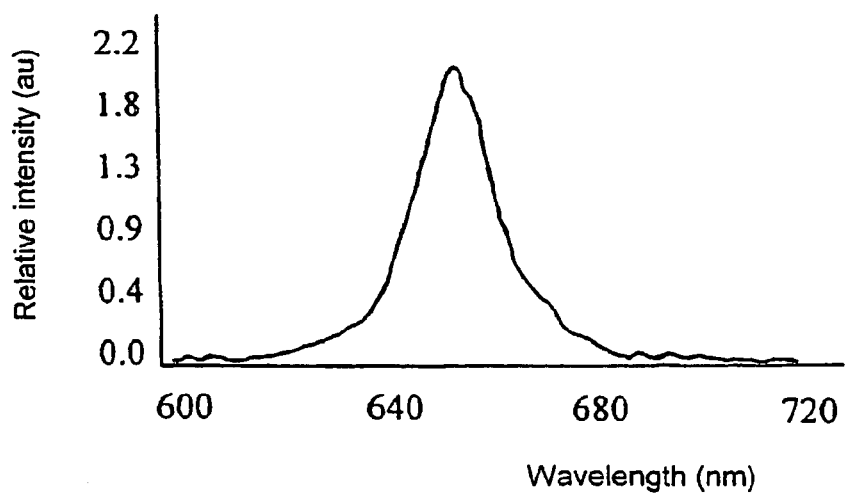
FIG. 5 is a graph showing the spectrum of a selected light beam.

The light source selector 50 contains several options for the user (such as choosing one from five). It includes several pre-set LEDs with fixed wavelength ranges. The spectrum of one is shown in FIG. 5. In which, its peak wavelength is 656 nm and its half-wave width is about 18 nm.

The detector 60 is a photo detector (such as the Si PIN photo detector) with the sensitivity about 0.50 A/W.

The diameter (D) of the circular recess 11 of the micro container 10 is 0.5 cm. And, its depth (H) is about 0.01 cm. Therefore, the total volume of the specimen 12 is only $(3.14 \times 0.5^2)/4 \times 0.01 \approx 0.002$ cc.

The installation of the entire system can be seen in FIG. 3. The related criteria are listed below:

About testing agent: a coloring agent (a blue soluble nanometer-degreed ball-typed agent) diluted with suitable amount of purified water filtered by a reverse-osmosis (R.O.) device.

Other items include:
(a) the testing liquid is filled in the micro container 10; and
(b) the final results of this embodiment are shown in FIGS. 6 and 7.

Figure 6:
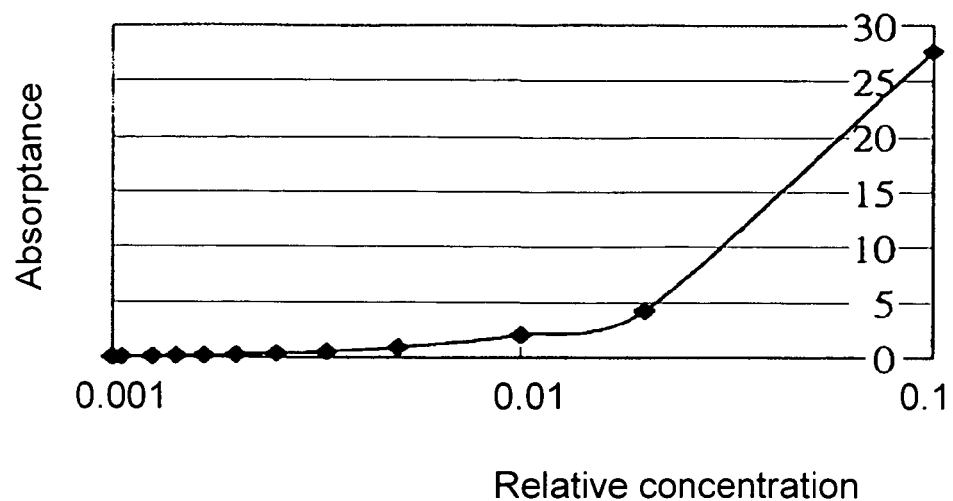
FIG. 6 is a graph showing the final result of a test.
Figure 7:
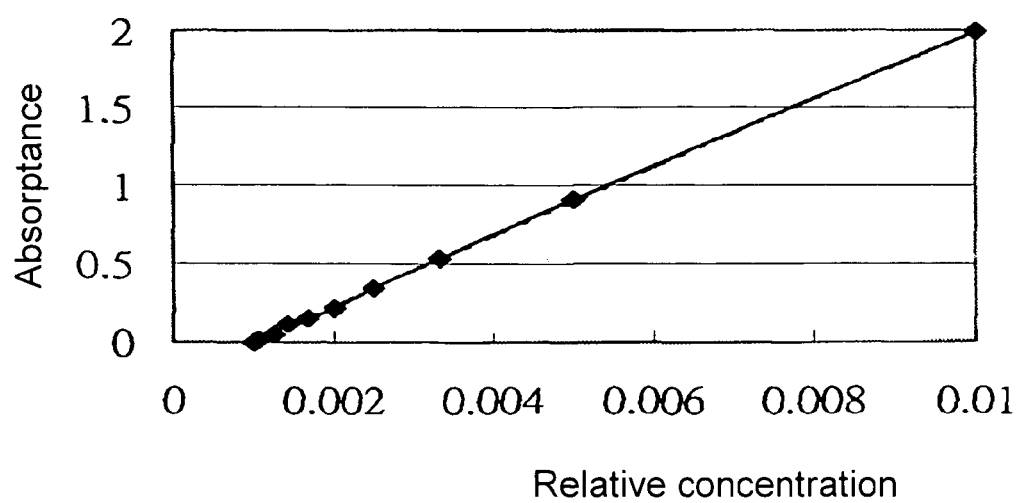
FIG. 7 is a graph showing a specific range of the final result.
Figure 8:
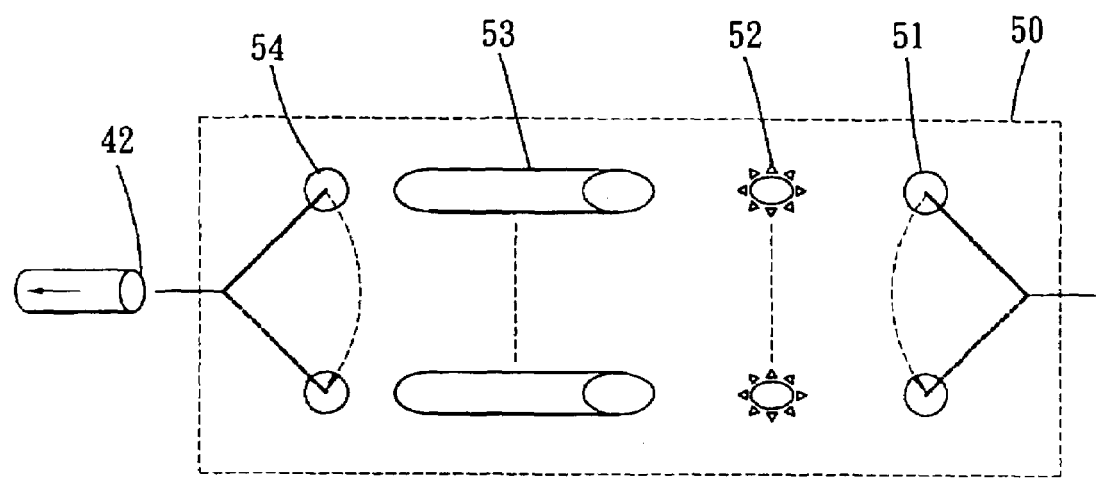
FIG. 8 is a schematic diagram for the light source selector.

Referring to FIG. 6 about the testing result, the density range between 1%~0.1% and another density range between 1%~10% are two straight lines with different slopes. If the density is smaller than 0.001% or higher than 10%, it will be beyond the range to be measured. Moreover, the enlarged relationship of the final result between 1%~0.1% is shown in FIG. 7.

Thus, if the detected value of the shade just falls in the reliable range, then its density can be determined accordingly from the known graph.

Therefore, the advantages and functions of this invention can be summarized as follows:

[1] the required volume of the specimen is small. Because the required volume of the specimen in the micro container is approximately 0.002 cc, it is significantly lower than the required 1 cc of the conventional one (almost 1/500 of the conventional one). That is, only a tiny volume of the specimen is possible to carry out a desired bio-chemical or medical test.

[2] the entire optic-electronic system is simple and at low cost. The system of the present invention is very simple. It can be manufactured as a device to detect certain virus, such as for a specific virus-detecting device, a particular material density detecting device, etc. Its commercial applications are unlimited.

[3] the precision will be doubled by the double path design. Due to the double path design, the beam will penetrate the specimen twice (forth and back) so that the entire sensitivity or precision will be doubled.

[4] By using the LEDs to avoiding the use of filter and solving the over-heating problem. In this invention, the selected beam will match the peak of the spectrum of the coloring agent. Therefore, there is no need to add an additional filter to filter out the unnecessary wavelength range(s). Thus, the filter is not required and the over-heating problem caused by the filter is eliminated.

[5] It can execute many bio-chemical tests. The user can select a desired beam from the light source selector 50 that is generated by one of the pre-set LED array 52 with a suitable wavelength range. So, such beam will match the coloring agent to have the best absorption effect. Thus, multiple bio-chemical tests are possible to be executed by this invention.

The above embodiments are only used to illustrate the present invention, not intended to limit the scope thereof. Many modifications of the above embodiments can be made without departing from the spirit of the present invention.

What is claimed is:

1. A double path microdrop optical biometric system comprising:
   a micro container, having a predetermined depth and a circular recess with a predetermined diameter for receiving a specimen, said micro container having a first end and a second end;
   a corner cube array disposed near the first end of said micro container, said corner cube array having a plurality of micro corner cubes so as to reflect an incoming beam back along its original path of said incoming beam;
   a collimator disposed at a position outside said second end of said micro container;
   a beam splitting device having an input fiber, an output fiber and a two-way fiber;
   a light source selector for providing a first beam having a predetermined wavelength range and intensity, said light source selector including an electrical switch, a LED array having a plurality of different colored LEDs, a plurality of middle fibers, and a light coupler to guide a selected colored light into the input fiber so that the first light beam having a desired wavelength;
   a detector for detecting a final intensity of a received beam; and
   a signal comparator unit for comparing said detected final intensity of said specimen with a reference intensity so that an absorptance of said specimen can be calculated;
   wherein said input fiber guides the first beam passing through said cube beamsplitter of said beam splitting device and then through said two-way fiber to arrive to said collimator so as to expand as a second beam having another diameter approximately equal to said predetermined diameter, then said second beam continues to penetrate said micro container and becomes a third beam, after reflected by said corner cube array and passing through said micro container again, a fourth beam is obtained; after passing through said collimator, said fourth beam becomes a collected fifth beam; said fifth beam enters said two-way fiber to arrive to said cube beamsplitter of said beam splitting device and then to be reflected aside into said output fiber and finally to said detector so that said signal comparator unit can calculate an absorptance of said specimen.

2. The double path microdrop optical biometric system as claimed in claim 1, wherein said micro container is an elongated transparent plastic plate and said circular recess has a diameter between 4 to 6 mm and a depth between 0.1 to 0.5 mm.

* * * * *